Figure 4:
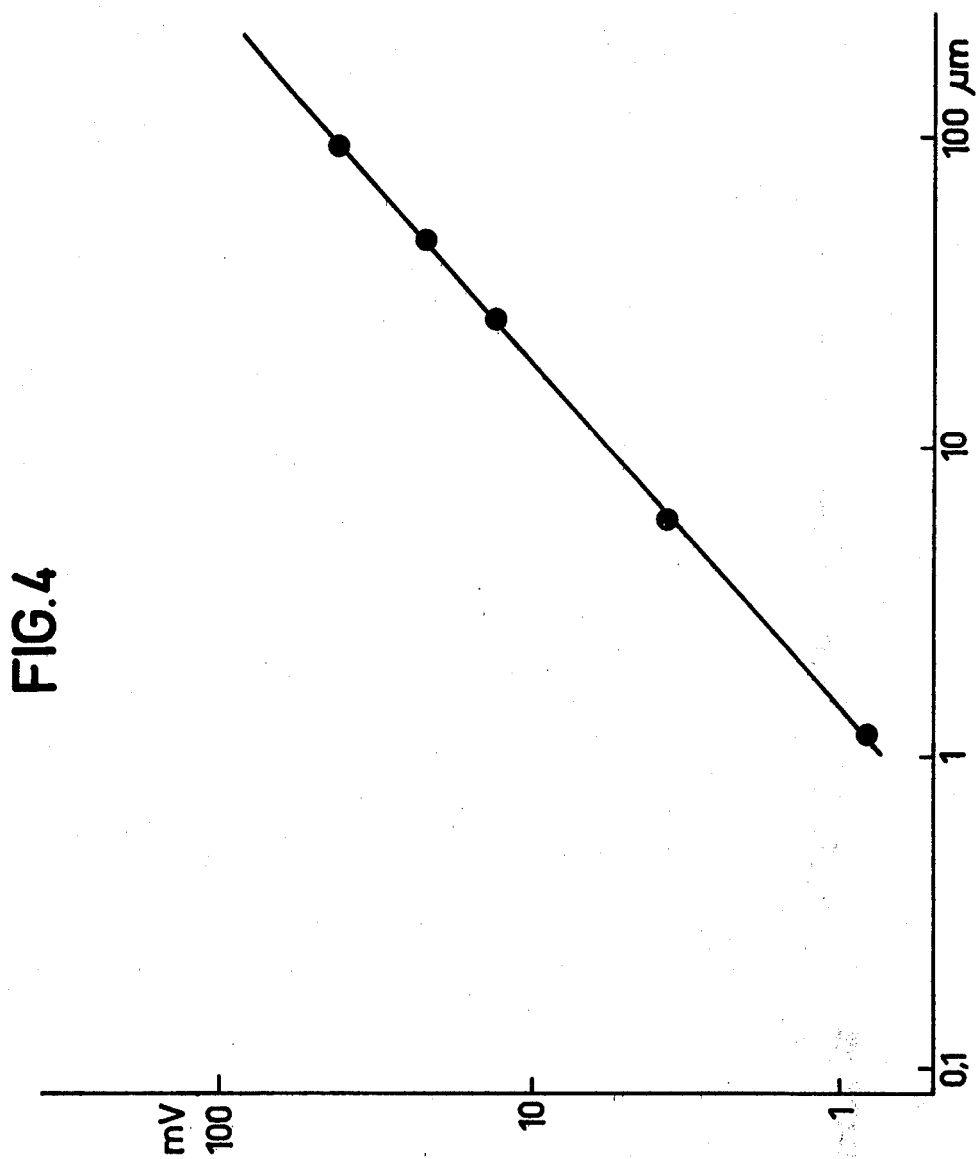

United States Patent [19]

Fladda et al.

[11] 4,420,256
[45] Dec. 13, 1983

[54] DUST MEASUREMENT

[75] Inventors: Gerdt Fladda; Thorulf Pettersson, both of Täby, Sweden

[73] Assignee: Svenska Träforskningsinstitutet, Stockholm, Sweden

[21] Appl. No.: 237,123

[22] PCT Filed: Jun. 13, 1980

[86] PCT No.: PCT/SE80/00172
§ 371 Date: Feb. 12, 1981
§ 102(e) Date: Feb. 12, 1981

[87] PCT Pub. No.: WO80/02876
PCT Pub. Date: Dec. 24, 1980

[30] Foreign Application Priority Data
Jun. 15, 1979 [SE] Sweden ............... 7905294

[51] Int. Cl.³ ........................................... G01N 15/02
[52] U.S. Cl. ................................... 356/336; 250/565; 250/574; 356/341; 356/343
[58] Field of Search ............... 356/336, 338, 341, 343; 250/564, 565, 574

[56] References Cited

U.S. PATENT DOCUMENTS 4,078,863  3/1978  Eriksson et al. ............... 356/336 X
4,110,044  8/1978  Pettersson et al. ............. 250/564 X
4,167,335  9/1979  Williams ........................... 356/336
4,193,692  3/1980  Wynn ................................ 356/341

FOREIGN PATENT DOCUMENTS 7513524-4  5/1977  Sweden .
7706318-8  11/1978  Sweden .
7706320-4  11/1978  Sweden .
7706319-6  12/1978  Sweden .

Primary Examiner—William L. Sikes
Assistant Examiner—Matthew W. Koren
Attorney, Agent, or Firm—Cushman, Darby & Cushman

[57] ABSTRACT

A method for measuring substantially spherical particles, such as dust. Two signals are formed, one of which is an approximately linear function of the particle concentration independently of the particle diameter and the second one is an approximately linear function of the particle diameter independently of the particle concentration. In order to obtain these signals the particles are illuminated with light in a direction different from their direction of flow. At least two detectors are arranged in such a way that the light in the beam path from the light source (3) to the first detector (6) is substantially only influenced by scattering and by light absorption of the particles and that the light in the beam path from the light source to the second detector (7) passes substantially only via reflections against the particles. The two signals are formed by definite relations between the d.c. voltage components of the output signals of the detectors and the average value of the squared R.M.S. value of the a.c. voltage component of the output signal from one of the detectors.

10 Claims, 4 Drawing Figures

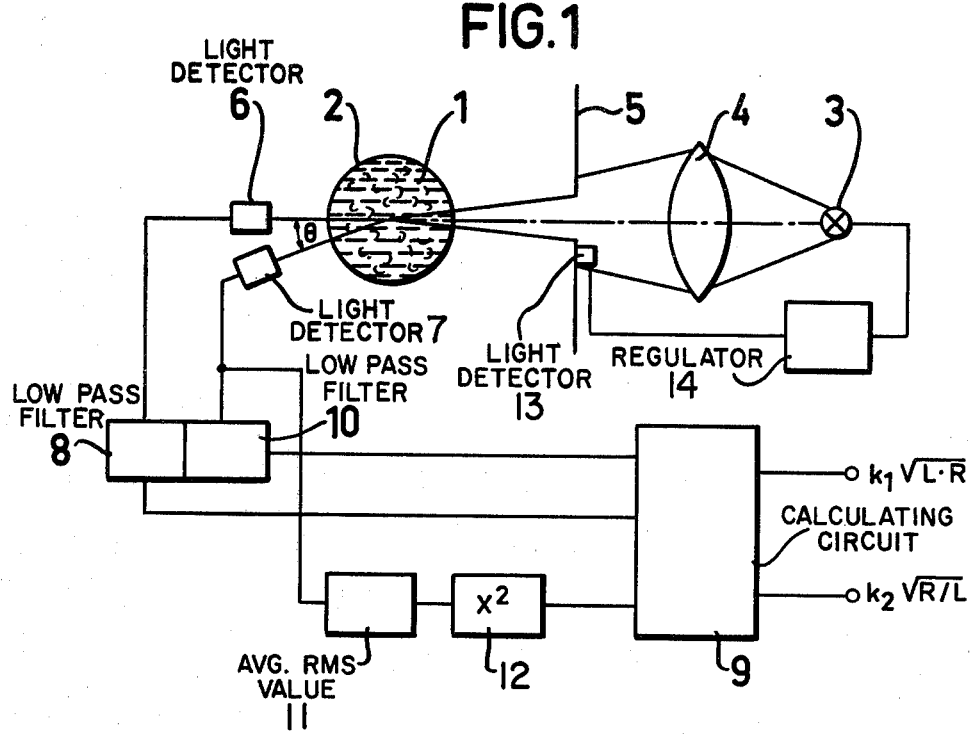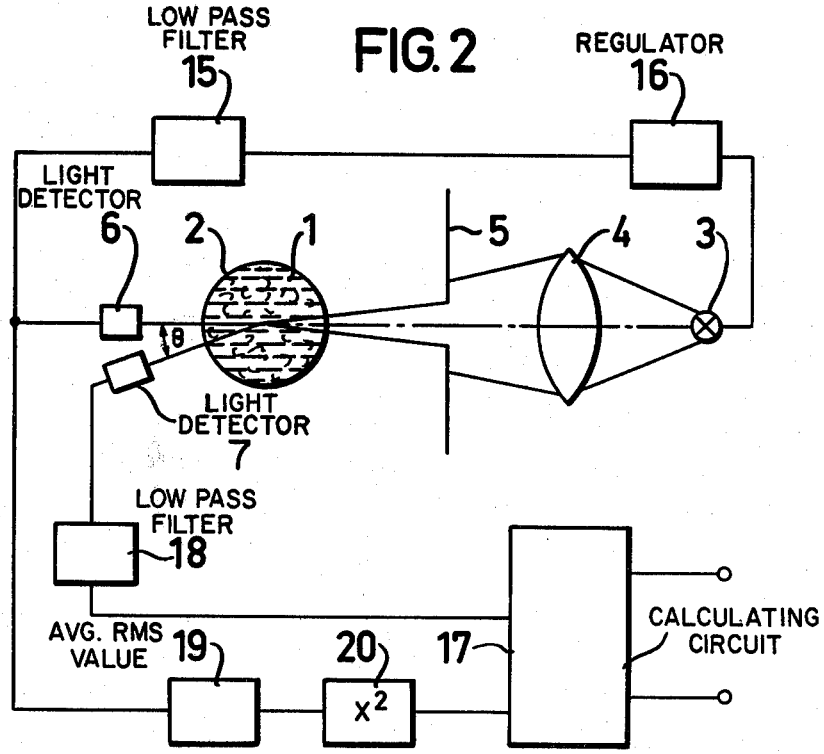

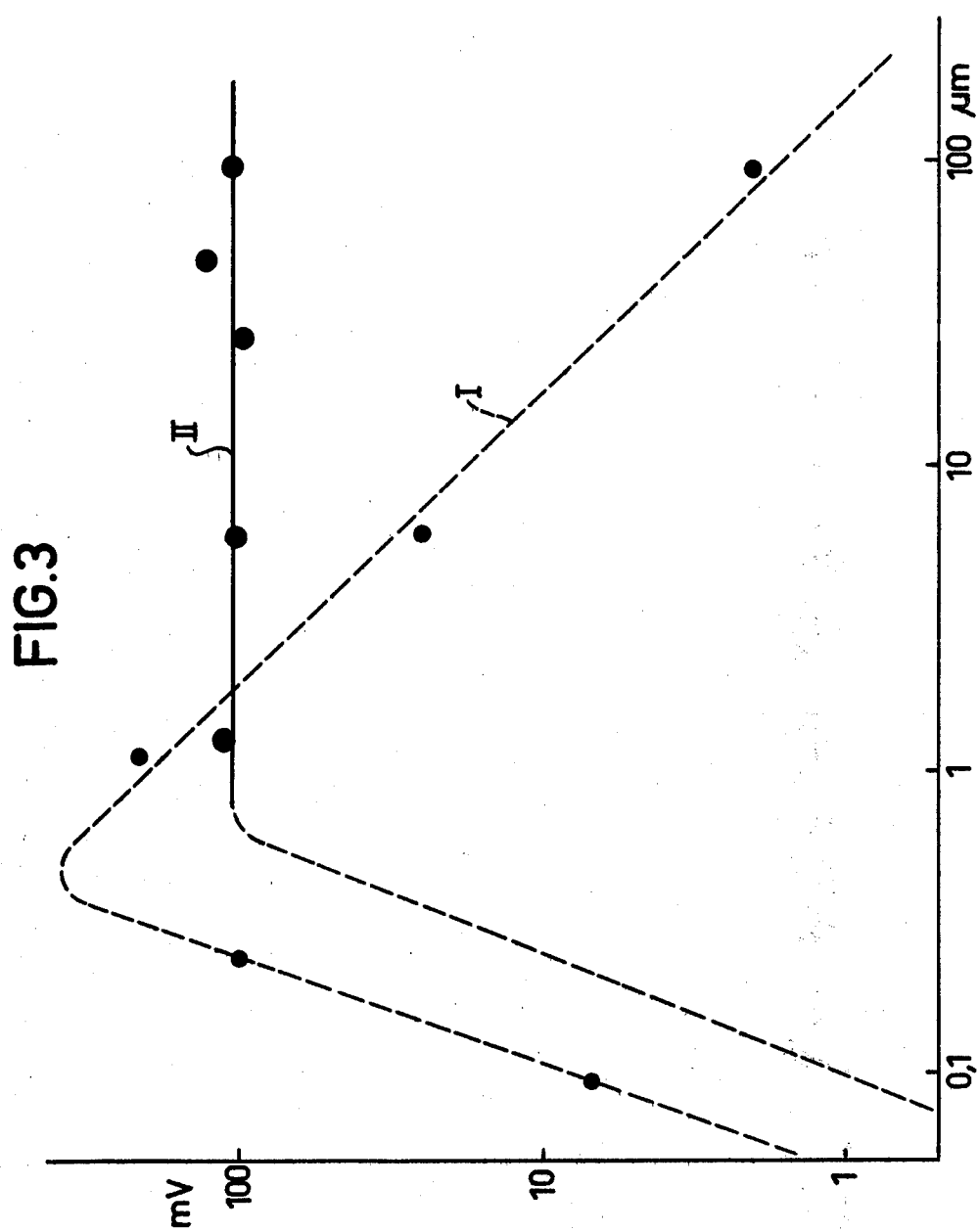

DUST MEASUREMENT

The present invention relates to a method for obtaining meaningful and utilizable electrical signals for measurements of flowing, substantially spherical particles (dust particles), using a light source which is adapted to illuminate the particles with light in a direction different from the direction of flow of the particles.

The environmental legislation and the process-technical development have led to an increased interest in instruments for continuous measurement of dust emissions. This applies to registration of the amount of emission to a recipient and to controlling its state as well as to supervision of operating conditions of dust emitters and the state of purification plants.

Existing instruments for continuous measurement of dust emission are substantially based on optical methods, where light used to illuminate a flowing medium containing particles is detected by a light detector disposed opposite the source of light. Otherwise a combined light source/detector unit is mounted at one end of the emission channel and the reflector unit at the opposite end. The damping of the light intensity caused by the dust is measured, and the obtained values is used as a measure of the particle concentration. However, damping will be considerably greater for fine particles than for large ones for the same mass concentration. Therefore, the correctness of the measurement values will be very dependent on the composition of the dust with respect to the particle size which often shows great variations.

The difficulties mentioned above are overcome by the invention. In accordance therewith, at least two light detectors are arranged in such a way that the light in the beam path from the light source to the first detector is substantially only influenced by as well loss by scattering as light absorption by the particles and this means that it is positioned on the opposite side of the sample from the light source on the axis of the incident beam, and that the light in the beam path from the light source to a second detector substantially only passes via reflections against the particles and this is provided by having the second detector positioned on the opposite side of the sample from the source on an axis angled with respect to the axis of the incident beam. Furthermore, the d.c. voltage component of the output voltage from the first detector related to the supply voltage to the light source is brought to act upon the d.c. voltage component of the output voltage from the said second detector, and the resultant signal is used to form a signal L. The a.c. voltage component from one of the said detectors is filtered out and the average value of the true R.M.S. value is formed and squared, and a signal R is formed on the basis of said squared average value of the true R.M.S. value. According to the invention, a signal $A = \sqrt{L \cdot R}$ proportional to the concentration and/or a signal $B = \sqrt{L/R}$ to the average particle diameter are formed and constitute the utilizable signals.

On one hand, the method according to the invention will give a measuring result of the amount of dust particles that is independent of the particle size and of the flow rate, and on the other hand a measuring result of the average diameter of the dust particles in the measuring sample will be obtained and will be independent of the amount of dust particles.

The method is founded on the basic signals and on the placing of the elements necessary for the method which are described in the Swedish patent specification 7706320-4. (This is a third Swedish addition to a parent application that has further more matured into e.g. U.S. Pat. No. 4,110,044, the subject matter of which is specifically incorporated herein by reference. A method for obtaining a measure of the concentration of particles suspended in a liquid is described in the Swedish patent specification. Said method is very well suited for measuring particles above a certain size whether they are suspended in a liquid or are gas-carried. The new method according to the invention especially utilizes the physical conditions existing when measuring spherical particles.

Moreover, the method is built on the use of the basic signals described in Swedish patent specification Nos. 7706318-8, 7706319-6 and the above-mentioned 7706320-0. (The first number refers to a first Swedish addition to the above-mentioned parent application, the second number refers to a second Swedish addition to said parent application, and the third number is the same one as is mentioned above.) The method according to the invention is adapted to measurement of concentration and/or average diameter of flowing spherical particles and is especially suited for measuring dust. Dust particles are often round. Although basic signals are used which are described in the above-mentioned patent specifications and which are more specifically referring to measurement of fibers, considerable research work has been spent on achieving an adaptation thereof to the said quite different conditions. The method according to the invention is strictly useful for measurement of particles having a particle size above the wavelength of the light used in the method.

The basic signals mentioned above are provided by illuminating the particles with light in a direction different from the direction of flow. In order to give a good conception of the motion of the particles, i.e. a well-defined a.c. signal from the detector, the radiation direction of the light, however, should be selected within a range from 90° to about 45° relative to the flow direction.

Two light detectors are used. One indicates, in a certain direction to the sample, light spread by the sample. The d.c. signal from this detector will then be substantially only dependent on light reflected from particles. The other detector indicates light transmitted straight through the sample, and the d.c. signal component from said detector will then be dependent on light scattered away by the particles in the sample. Both said signals are in a similar degree dependent on the light absorption in the sample. One possibility is then that the intensity of the light source is maintained on a defined and constant level, and the d.c. signal components from the two detectors are divided by each other, giving the signal L according to equation (1) below. Approximate simplifications thereof are also possible.

$$L = \ln\left[\left(\frac{V_{DC(\theta°)}}{V_{DC(0°)}} - \frac{V'_{DC(\theta°)}}{V'_{DC(0°)}}\right)/c_1 + 1\right] \quad (1)$$

Where $V_{DC(\theta°)}$ is the d.c. voltage component of a signal from a detector placed in the angular position $\theta°$ when measuring on a sample, $V_{DC(0°)}$ is the d.c. voltage component of a signal from a detector placed in the angular position 0° when measuring on a sample, $V_{DC(0°)}'$ and $V_{DC(\theta°)}'$ are d.c. voltage signals from the two detectors, respectively, when the emission does not contain dust particles. $c_1$ is a constant.

Another possibility is that the d.c. voltage signal from the detector giving a d.c. voltage signal is substantially dependent on the light scattering and on the light absorption in the sample, and that the intensity of the light source is so adjusted that the d.c. voltage signal from this detector will be continuously maintained constant. Even in this case a signal L is formed, but this signal is formed according to the following equation (2):

$$L = \ln\left[\frac{V_{DC(\theta°)} - V'_{DC(\theta°)}}{c_3} + 1\right] \quad (2)$$

wherein $c_3$ has been so selected that $V_{DC(\theta°)} = 1$ for only air in the channel.

In both said embodiments also the a.c. voltage component from one of the detectors (it is unimportant which one) is calculated, and the average R.M.S. value $V_{RMS}$ thereof is formed and is squared and used to form a signal R according to the following equation (3) or an approximate value thereof $$R = \ln\left[\frac{V_{RMS}^2}{c_2} \cdot \frac{V'^2_{DC(0°)}}{V^2_{DC(0°)}} + 1\right] \quad (3)$$

wherein $c_2$ is a constant.

The investigation of what properties are really measured by the signals mentioned above continued after the filing of the previously mentioned background patent specifications. These investigations have shown that the signal L is proportional to the concentration of the particles and inversely proportional to the average radius r, i.e. $L \sim \text{conc.} \cdot 1/r$. The signal R is proportional to as well the average length q of the particles in the direction of flow and to their concentration.

The realizing of these connections led to the idea according to the invention that the signals mentioned above also could be used for measuring of spherical particles, such as dust, because for spherical particles $a = 2r$, resulting in $R \sim \text{conc.} \times r$. It follows from this that:

$$A = \sqrt{L \cdot R} \sim \text{conc.},$$

thus independent of the particle diameter $$B = \sqrt{R/L} \sim r,$$

thus independent of the concentration

Although the invention is described with reference to measurement on dust, it is quite obvious that it is not limited to this purpose, but is equally useful when measuring spherical particles, in whatever medium these are present. Since the result of the measurements, moreover, will be fully independent of the flow, the particles need not be in a medium, either, which is flowing itself, but the method is also very well suited for measurement on e.g. sedimented particles.

The invention will be described in the following more in detail with reference to the attached drawings, on which FIGS. 1 and 2 show two different embodiments for carrying out the invention, FIG. 3 shows a diagram of the output signal as a function of the particle diameter of spherical model particles having a definite concentration, on the one hand for a device according to the invention and on the other hand for a commercial dust measuring instrument based on light scattering technique according to the state of the art, and FIG. 4 shows a diagram of the output signal from the device according to the invention, where the diameter output signal is shown as a function of the diameter of the model particles (latex particles).

In FIG. 1 a first embodiment for carrying out the method according to the invention is shown. Dust 1 travels through a measuring channel 2 having walls transparent to the light used, e.g. consisting of glass. The measuring channel is preferably circular-cylindrical in order to give a radiation passage perpendicular to the wall of the measuring channel, but other forms are also possible, such as square ones. It is also quite possible to have a light source with optics and light detectors situated within the measuring channel. A light source 3 illuminates the dust 1 via an optical arrangement, here shown schematically consisting of a lens 4 and a diaphragm 5 focusing a well-defined beam in the centre of the measuring channel.

a light detector 6 is located straight opposite to the light source 3 on the optical axis on the other side of the measuring channel, and at a certain angle $\theta$ to the optical axis with the focusing point as a centre, where another light detector 7 is situated. The signal obtained from the detector 6 is fed to a low-pass filter 8 filtering out the a.c. voltage component of the signal. The d.c. voltage component of the signal from the detector 6 obtained from the filter is fed to an input of a calculating unit 9. The output signal from the detector 7 is fed to a low-pass filter 10 of the same type as the filter 8 and also to a unit 11 forming a signal representing the average value of the R.M.S. value of the a.c. voltage component of the signal from the detector 7. The output signal from the filter 10 is fed to a second input on the calculating unit 9 and the output signal from the unit 11 is via a squaring circuit 12 fed to a third input on the calculating unit 9.

The calculating unit 9 transforms the three incoming analogue signals into their digital counterparts, calculates the above-mentioned basic signals L and R and calculates the signal $\sqrt{L \cdot R}$, proportional to the concentration and delivers a signal proportional to said signal from one of its outputs. Moreover, it calculates the signal $\sqrt{R/L}$, proportional to the average diameter of the dust particles and delivers a signal proportional to said further signal from its other output.

A third light detector 13 is placed on the diaphragm 5 close to the aperture within the radiation cone from the light source 3. The detector 13 records the intensity variations of the light source and compensates for these via a regulator 14 connected to the light source. However, this adjustment is not absolutely necessary. As a matter of fact it is only necessary if an absorption measurement of the type indicated in Swedish patent specification 7706319-6 has to be carried out.

FIG. 2 shows a second embodiment for carrying out the method according to the invention. The embodiment and the location of the elements 1 to 7 and 13 corresponds to that of the corresponding elements in FIG. 1. However, as distinguished from the embodiment according to FIG. 1, the d.c. voltage component of the signal from the light detector 6 is used for adjusting the light source 3. Therefore, the output signal from the detector 6 is fed via a low-pass filter 15 to the regulator 16.

The intensity of the light source will then be dependent on the light absorption and the light scattering at the dust in such a way that the light source will emit stronger light the higher the absorption is of the dust. In this way an automatic compensation of the absorption is also achieved for the signal detected by the light detector 7 and, more specifically, in such a way that the calculating unit can form the signal L directly from the filtered d.c. voltage component of the signal obtained from the detector 7.

In the device shown in FIG. 2 the a.c. voltage component of the signal is derived from the detector 6 instead of the detector 7 as in FIG. 1. A signal corresponding to the square of the R.M.S. value is formed and fed to a third input on the circuit 17 as a signal R.

It principle it is of no importance if the a.c. voltage component is derived from the detector 6 or the detector 7, the variation of the light produced by the flowing dust due to the light absorption of the dust or due to its scattering of the light only differing by a constant factor.

In practice, so low signal levels are obtained when measuring dust that only the detector 7 can be used for recording the a.c. voltage component. Noise from the light source will otherwise drown the signal from the detector 6.

In FIG. 3 a dashed curvre I shows the measuring results obtained by a commercial dust measuring instrument based on common light scattering technique as a function of the particle size of a constant concentration of 25 mg/l. As is apparent this instrument is extremely responsive to the particle size. The strong decrease in sensitivity with the particle size will appear when the wavelength is less than or about equal to the particle size. There is no method known for compensating said decrease. However, knowledge about dust composition etc. can in certain cases give emprical compensation possibilities. In principle it can be said that a light wavelength should be selected that is smaller than the smallest particle size which is of importance when determining the dust content. However, this is not always possible in practice, as light sources with too short a wavelength cannot be used.

In FIG. 3 also a full drawn curve II is shown representing the result obtained by the method of the invention. Also in this case the output signal of the instrument is presented as a function of the particle size of a constant concentration of 25 mg/l. The beginning of the curve, for dust particle sizes below the light wavelength of the light used and generated by an IR-diode forming a light source is rising as for the curve 1 obtained by a common instrument, but for particle sizes in excess of this the curve II will constantly keep the same level. The result clearly indicates that the method of the invention is independent of the dust particle size when the particles are larger than or about equal to the wavelength.

The curves shown have been obtained by feeding samples of different particles sizes through the measuring device. In doing so the particle sizes of every measurement have been maintained within a well-defined size range. They are not exactly so ideal in measurement of dust in a dust emission, as in practice a dust emission contains dust particles distributed over a large size area with a distribution curve which is specific to each type of dust on which the measurement is performed.

Tests have shown that the result of a measurement carried out with a dust measuring device built according to the principle of the invention is dependent to a certain extent, however, very small on the size distribution of the dust, i.e. is variance dependent. To compensate for this, a series of measurements can be made at each installation of a dust measuring device according to the invention under simultaneous manual sampling of the dust and determination of its concentration in a laboratory. Curves can be drawn for the result obtained by the instrument and the result obtained from the sampling as a function of the signal of the average diameter of dust particles at each measuring occasion. Provided the deviation between these curves gives an unambiguous deviation for each average diameter, an empirical correction can be introduced in the calculating unit of the value obtained by the instrument to coincide with the value obtained from the manual sampling. Thus, the calculating unit performs the calculation of the signal A described above and adds or subtracts a correction value specific to each calculation value or performs a correction by a special correction factor.

In FIG. 4 the diameter signal obtained with the method of the invention is shown as a function of the correct size of the dust particles. As is evident the measurement result lies on a straight line and indicates the possibilites of the method for measuring the composition of the dust with respect to the particle size.

We claim:

1. Measuring apparatus for measuring the concentration of and/or average particle diameter of substantially spherical particles present in a flowing medium, comprising:

a light source for illuminating the particles with a light beam having an axis in a direction different from the direction of flow of the medium;

a first light detector, positioned along the axis of the light beam so as to receive light not scattered and not absorbed by the particles, for generating, responsive to the amount of light detected thereby, a first light detector signal having DC and AC components;

a second light detector, positioned not along the axis of light beam so as to only receive light reflected by the particles, for generating, responsive to the amount of light detected thereby, a second light detector signal having DC and AC components;

a first low pass filter, coupled to said second light detector, for filtering out the AC component of said second light detector signal and passing only the DC component thereof;

RMS circuit means, coupled to one of said first and second light detectors, for generating a signal related to the average RMS value of the AC component of the light detector signal received therefrom;

squaring circuit means, coupled to the RMS circuit means, for generating a signal related to the square of the average RMS value of the AC component coupled to said RMS circuit means; and a calculating circuit, coupled to said squaring circuit means and to said first low pass filter for (a) generating a first signal L representing a logarithmic function of the DC voltage component of the output voltage from the second detector proportional to the concentration of the particles and inversely proportional to the average radius of the particles, (b) generating a signal R representing a logarithmic function of said squared average RMS value proportional to both the average radius of the particles and to the concentration of the particles, (c) generating a first signal $A = \sqrt{L \cdot R}$ proportional to the concentration and independent of the particle diameter when measuring the concentration, and (d) generating a second signal $B = \sqrt{R/L}$ proportional to the diameter of the particles and independent of their concentration when measuring the average particle diameter.

2. A measuring apparatus according to claim 1 further comprising:

a third light detector positioned so as to receive light directly from said light source without any interference by said particles, for generating an intensity signal related to the intensity of said light source;

a regulator, coupled to said third light detector so as to receive said intensity signal, for feeding back a signal to said light source and adjusting the intensity thereof so as to render the output of said third light detector constant; and a second low pass filter, coupled to said first light detector, for filtering out the AC component of said first light detector signal and passing only the DC component thereof; and wherein said calculating circuit is coupled to both low pass filters and to said squaring circuit means and generates said L signal in accordance with the equation $$L = \ln\left[\left(\frac{V_{dc}(\theta°)}{V_{dc}(0°)} \cdot \frac{V'_{dc}(\theta°)}{V'_{dc}(0°)}\right) / C_1 + 1\right]$$

wherein $V_{dc}(\theta°)$ is the DC component of the second light detector signal when measuring a sample containing particles, $V_{dc}(0°)$ is the DC component of the first light detector signal when measuring a sample containing particles, $V'_{dc}(0°)$ is the DC component of the second light detector signal when measuring a sample containing no particles, $V'_{dc}(\theta°)$ is the DC component of the first light detector signal when measuring a sample containing no particles, and $C_1$ is a constant.

3. A measuring apparatus according to claim 1 wherein said calculating circuit generates said R signal according to the equation $$R = \ln\left[\frac{V^2_{RMS}}{C_2} \cdot \frac{V'^2_{dc}(0°)}{V^2_{dc}(0°)} + 1\right]$$

wherein $V_{RMS}$ is the average of the RMS value of the AC component as determined by said RMS circuit means, $V'_{dc}(0°)$ and $V_{dc}(0°)$ are the DC components of said first light detector signal when measuring samples containing no particles and particles, respectively, and $C_2$ is a constant.

4. A measuring device according to any of claims 1, 2, or 3, further comprising:

means for storing correction values within said calculating circuit related to various types of particles to be measured and wherein the appropriate correction value is added or subtracted to the value of A and B by said calculating circuit.

5. A measuring apparatus according to claim 1 further comprising:

a second low pass filter, coupled to the output of said first detector for blocking the AC component of the first light detector signal and passing only the DC component thereof; and a regulator, coupled to said second low pass filter so as to receive the DC component of the first light detector signal for feeding back a signal to said light source for adjusting the intensity thereof so as to render the DC component of the first light detector signal constant, wherein said calculating circuit generates said L signal according to the equation $$L = \ln\left[\frac{V_{dc(\theta°)} - V'_{dc(\theta°)}}{C_3} + 1\right]$$

where $V_{dc(\theta°)}$ is the DC component of said second light signal when measuring a sample containing particles, $V'_{dc(\theta°)}$ is the DC component of said second light signal when measuring a sample containing no particles, and $C_3$ is a constant.

6. A method for measuring the concentration of and/or average particle diameter of substantially spherical particles present in a flowing medium, comprising the steps of:

(a) illuminating the particles with a light beam having an axis in a direction different from the direction of flow of the medium;

(b) generating, with a first light detector, positioned along the axis of the light beam so as to receive light not scattered and not absorbed by the particles, a first light detector signal related to the amount of light detected thereby, the first light detector signal having AC and DC components;

(c) generating, with a second light detector, positioned at a point not along the axis of the light beam so as to only receive light reflected by the particles, a second light detector signal related to the amount of light detected thereby, the second light detector signal have DC and AC components;

(d) low pass filtering said second light detector signal so as to block the AC component and pass only the DC component thereof;

(e) generating an RMS signal indicative of the RMS value of the AC component of one of said first and second light detector signals;

(f) generating a squared signal indicative of the squared value of the RMS signal; and (g) generating a first signal L representing a logarithmic function of the DC voltage component of the second light detector signal proportional to the concentration of the particles and inversely proportional to the average radius of the particles;

(h) generating a second signal R representing a logarithmic function of said squared average RMS value proportional to both the average radius of the particles and to the concentration of the particles;

(i) generating a first signal $A = \sqrt{L \cdot R}$ proportional to the concentration and independent of the particle diameter when measuring the concentration; and (j) generating a second signal $B = \sqrt{R/L}$ proportional to the diameter of the particles and independent of their concentration when measuring the average particle diameter.

7. A method for measuring according to claim 6, further comprising the steps of:

(k) generating, with a third light detector positioned so as to receive light directly from said light beam without any interference by said particles, an intensity signal related to the intensity of said light beam;

(l) feeding back said intensity signal so as to regulate the intensity of said light beam to produce a constant intensity signal; and (m) low pass filtering said first light detector signal so as to block the AC component and pass only the DC component thereof; and wherein said L signal is generated according to the equation $$L = \ln\left[\left(\frac{V_{dc}(\theta°)}{V_{dc}(0°)} \cdot \frac{V'_{dc}(\theta°)}{V'_{dc}(0°)}\right)/C_1 + 1\right]$$

wherein $V_{dc}(\theta°)$ is the DC component of the second light detector signal when measuring a sample containing particles, $V_{dc}(0°)$ is the DC component of the first light detector signal when measuring a sample containing particles, $V'_{dc}(0°)$ is the DC component of the second light detector signal when measuring a sample containing no particles, $V'_{dc}(\theta°)$ is the DC component of the first light detector signal when measuring a sample containing no particles, and $C_1$ is a constant.

8. A method for measuring according to claim 6 wherein said R signal is generated according to the equation:

$$R = \ln\left[\frac{V^2_{RMS}}{C_2} \cdot \frac{V'^2_{dc}(0°)}{V^2_{dc}(0°)} + 1\right]$$

$V_{RMS}$ is the average of the RMS value of the AC component as determined by said RMS circuit means, $V'_{dc}(0°)$ and $V_{dc}(0°)$ are the DC components passed by said first low pass filter when measuring samples containing no particles and particles, respectively, and $C_2$ is a constant.

9. A method for measuring according to claim 6, 7, or 8, further comprising the step of storing correction values within said calculating circuit related to various types of particles to be measured and correcting the values of A and B in accordance therewith.

10. A method for measuring according to claim 6, further comprising the steps of:

(k) low pass filtering said first light detector signal so as to block the AC component and pass only the DC component thereof; and (l) generating an intensity signal related to the DC component of said first light detector signal; and (m) feeding back said intensity signal so as to regulate the intensity of said ligght beam to produce a constant, intensity signal, and wherein said L signal is generated according to the equation $$L = \ln\left[\frac{V_{dc(\theta°)} - V'_{dc(\theta°)}}{C_3} + 1\right]$$

wherein $V_{dc(\theta°)}$ is the DC component of said second light signal when measuring a sample containing particles, $V'_{dc(\theta°)}$ is the DC component of said second light signal when measuring a sample containing no particles, and $C_3$ is a constant.

* * * * *